United States Patent
Warner et al.

(10) Patent No.: US 10,856,758 B2
(45) Date of Patent: Dec. 8, 2020

(54) INTRACARDIAC LOCALIZATION AND GUIDANCE SYSTEM AND METHOD

(71) Applicant: General Electric Company, Schenectady, NY (US)

(72) Inventors: Adrian F. Warner, Wauwatosa, WI (US); Claudio Patricio Mejia, Wauwatosa, WI (US); Daniel Richard Schneidewend, Wauwatosa, WI (US); Rodger F. Schmit, Wauwatosa, WI (US); Nicholas P. Nekich, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 795 days.

(21) Appl. No.: 14/586,195

(22) Filed: Dec. 30, 2014

(65) Prior Publication Data

US 2016/0184028 A1  Jun. 30, 2016

(51) Int. Cl.

| | |
|---|---|
| *A61B 5/0432* | (2006.01) |
| *A61B 5/00* | (2006.01) |
| *A61B 5/042* | (2006.01) |
| *A61B 5/06* | (2006.01) |
| *A61B 34/20* | (2016.01) |
| *A61B 18/14* | (2006.01) |
| *A61B 18/12* | (2006.01) |
| *A61B 5/044* | (2006.01) |
| *A61B 18/00* | (2006.01) |

(52) U.S. Cl.
CPC .......... *A61B 5/0432* (2013.01); *A61B 5/0422* (2013.01); *A61B 5/061* (2013.01); *A61B 5/6858* (2013.01); *A61B 34/20* (2016.02); *A61B 5/044* (2013.01); *A61B 18/1206* (2013.01); *A61B 18/1492* (2013.01); *A61B 2018/00577* (2013.01); *A61B 2034/2053* (2016.02)

(58) Field of Classification Search
CPC . A61B 18/1206; A61B 18/1492; A61B 5/061; A61B 5/6858; A61B 5/044
USPC ........................................................... 606/34
See application file for complete search history.

(56) References Cited

U.S. PATENT DOCUMENTS 5,876,336 A * 3/1999 Swanson ................. A61N 1/06
  600/374
6,511,478 B1 * 1/2003 Burnside ............ A61B 18/1492
  600/549
6,658,285 B2 12/2003 Potse et al.
(Continued)

FOREIGN PATENT DOCUMENTS

| CN | 202681984 | 1/2013 |
|---|---|---|
| WO | 2012048988 | 4/2014 |

*Primary Examiner* — Michael W Kahelin
*Assistant Examiner* — Minh Duc G Pham
(74) *Attorney, Agent, or Firm* — Fletcher Yoder, P.C.

(57) ABSTRACT

In the present invention, a system that has a navigation signal delivered by one of a signal or navigation catheter or treatment catheter as directed by a controller for detection by the other of the navigation catheter or the a treatment catheter to navigate the treatment catheter to a specific point or area of interest using the detected navigation signal is provided. The system is operable in a method to perform the above utilizing the mapping function of the electrophysiology mapping and/or recorder system to energize electrodes on either the navigation catheter or treatment catheter to direct the treatment catheter to the area, region or point of interest.

11 Claims, 3 Drawing Sheets

(56) References Cited

U.S. PATENT DOCUMENTS

| | | |
|---|---|---|
| 7,123,954 B2 | 10/2006 | Narayan et al. |
| 7,933,167 B2 | 4/2011 | Jean et al. |
| 8,731,641 B2 | 5/2014 | Hartmann et al. |
| 2007/0021679 A1 | 1/2007 | Narayan et al. |
| 2007/0208923 A1 | 9/2007 | Russell |
| 2011/0112396 A1* | 5/2011 | Shachar ................ A61B 34/70 600/424 |
| 2012/0130569 A1 | 5/2012 | Huntsberger et al. |
| 2013/0030482 A1 | 1/2013 | Warner et al. |
| 2013/0274582 A1* | 10/2013 | Afonso ................ A61B 5/0044 600/374 |

* cited by examiner

INTRACARDIAC LOCALIZATION AND GUIDANCE SYSTEM AND METHOD

BACKGROUND OF INVENTION

The subject matter generally relates to a system and method of electrical current detection, and more particularly to a system and method of electrical current detection for navigating a catheter during a medical procedure, such as an ablation procedure.

When performing procedures of varying types, it is often necessary to track or navigate a device through the body of the patient in order to reach the area of interest for the procedure. These devices can take the form of catheters that are inserted into the body of the patient and moved along the vascular system of the patient in order to reach the tissue of interest in the body. Without some form of navigation, it becomes a challenge to locate the region of interest relative to the patient's physical anatomy. Even using imaging techniques to identify the position of the actual catheters still leaves resolving the point of interest to significant variation.

Conventional electro-anatomical mapping systems currently in use can provide the desired navigation using magnetic and/or impedance navigation tracking methods for the determination of the position of these devices, such as a single or multiple catheters. A combination of both methods is also employed to improve the accuracy of the navigation of the devices within the body, and in particular with regard to navigation of a catheter in and around the heart, such as for ablation procedures.

These methods are advantageous in so far as they enable navigation within the entire chamber of the heart with accuracy better than +/−2.5 mm. In fact these methods can be used to map the entire chamber allowing conduction paths within the entire surface area of the chamber to be captured and observed by the user.

However, both methods are expensive in terms of requiring custom consumables, e.g., active catheters, thus an economic burden on the implementation and performance off the procedure, as well as a capital cost in terms of design implementation. In addition, while the accuracy of the navigation using these methods is high, in certain procedures, including ablation procedures, it is desirable to have a higher degree of accuracy than can be achieved with these prior art methods.

Accordingly, it is desirable to provide a navigation system and method that enables a clinician to guide a device, such as a catheter, to a particular region of interest in the body of a patient with improved accuracy and effectiveness of the treatment performed by the catheter.

BRIEF DESCRIPTION OF THE INVENTION

There is a need or desire for a system to navigate a treatment catheter, such as an ablation catheter, with greater precision to a specific region or area to be treated for more efficient and effective treatment of the patient. The above-mentioned drawbacks and needs are addressed by the embodiments described herein in the following description.

In exemplary embodiments of the invention, the system and associated method enables micro-localization and guidance of a catheter relative to a region of interest as determined from a conventional 2D or 3D mapping system, or through an electrophysiology (EP) recording and/or mapping system using a combination of traditional imaging and injected signal detection methodology. In this system and method, by employing two or more catheters as a signal or navigation catheter and a treatment catheter, which can take the form of traditional catheters and/or a basket catheter, it is possible to identify the region of interest using the signal catheter in the EP recording system and navigate the treatment catheter within that region using signals from the signal catheter to identify a specific location to terminate an arrhythmia using the treatment catheter. In particular, the system employs locations provided by the EP recording system and signal catheter to direct the treatment catheter to a specific treatment area adjacent or around the region of interest by using signals to locate the treatment catheter relative to the signal catheter. These signals may be in addition to, or in place of the signals to stimulate the tissue, i.e., the heart. Upon reaching the region of interest, the treatment catheter receives a signal from the signal catheter indicative of the position of the treatment catheter relative to the signal catheter. Based on the position and/or strength of the detected signal, the treatment catheter can be moved or navigated to a specific point within the region of interest at which location the treatment catheter can be utilized to treat a condition at the point of interest, such as by ablating tissue at that point to treat an arrhythmia. As a result the use of the EP navigation and injected signal detection in combination with one another in the system of the present invention, the system and method eliminates the need of a separate mapping system, or any other arrhythmia location device or system.

In other exemplary embodiments of the system and method of the invention the need for active catheters, such as catheters incorporating a search coil semiconductor equivalent, is eliminated such that the system is operable with only standard, low cost catheters, to reduce the cost of operation of the system.

In still other exemplary embodiments of the system and method to use traditional imaging techniques, such as an x-ray, to navigate the treatment catheter to the approximate anatomical area, where the system can then be utilized to provide effective site-specific navigation around and into the region of interest. In prior art magnetic navigation systems, these systems suffer calibration issues with any metal component that is associated with the patient, typically the XRAY system. However, the micro navigation system of the present invention is not affected by metal interference as there is no magnetic tracking component.

In still further exemplary embodiments of the system of the invention, the system also has the advantage of utilizing an existing EP recording system with a constant current signal generator and switch to allow the stimulator switching network to be used for navigation in the system of the invention via the signal catheter. In addition, with the system of the invention, no additional mapping/navigation system is required, and the system can be operated quickly to converge onto a small area under navigation analysis. Further, the system of the present invention can be streamlined into the procedural workflow, and no patient patch(es) or receiving antenna is required to operate the system.

In still another exemplary embodiment of the method of the invention, a method of navigating a treatment catheter to treat a region of interest in a body of a patient is provided comprising the steps of directing a navigation signal through a navigation catheter of an electrophysiology mapping system to be detected by a treatment catheter near the region of interest defined by the navigation catheter, determining an actual position of the treatment catheter based on the detection of the signal by the treatment catheter, comparing the actual position of the treatment catheter to the position of the navigation catheter and optionally moving the treatment catheter to position the treatment catheter at the region of interest based on the difference in the actual position of the treatment catheter from the navigation catheter.

In still another exemplary embodiment of the method of the invention, a system that has a navigation signal delivered by a signal or navigation catheter directed by a controller for detection by a treatment catheter to navigate the treatment catheter to a specific point or area of interest using the detected navigation signal is provided. The system performs the above utilizing the mapping function of the electrophysiology recorder system to energize the navigation catheter to direct the treatment catheter to the desired location.

In still another exemplary embodiment, system to navigate a treatment catheter to an area of interest to be treated in a body of patient, the system including a navigation catheter including a number of first electrodes thereon positionable around the area of interest, a treatment catheter including a number of second electrodes thereon, and a controller including a signal detection structure configured to detect and determine the location of a navigation signal, the controller operably connected to the navigation catheter and the treatment catheter to selectively energize at least one of the first electrodes or the second electrodes to emit the navigation signal and enable the treatment catheter to moved towards the area of interest bounded by the number of first electrodes.

According to yet another embodiment of the subject matter described herein, a method of directing a navigation signal to direct an ablation catheter to a location within a subject's heart is provided. The method can include the steps of communicating the navigation signals through an electrophysiology mapping system for delivery by a navigation catheter or the ablation catheter to the heart of a subject, creating an anatomical map of the location of an area of interest within the subject's heart, creating a display at an electrophysiology recorder that includes an illustration of the anatomical map of the area of interest, and energizing electrodes on one of the navigation catheter or the ablation catheter for illustration on the display and detection by the other of the navigation catheter or the ablation catheter to direct the ablation catheter to the area of interest.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
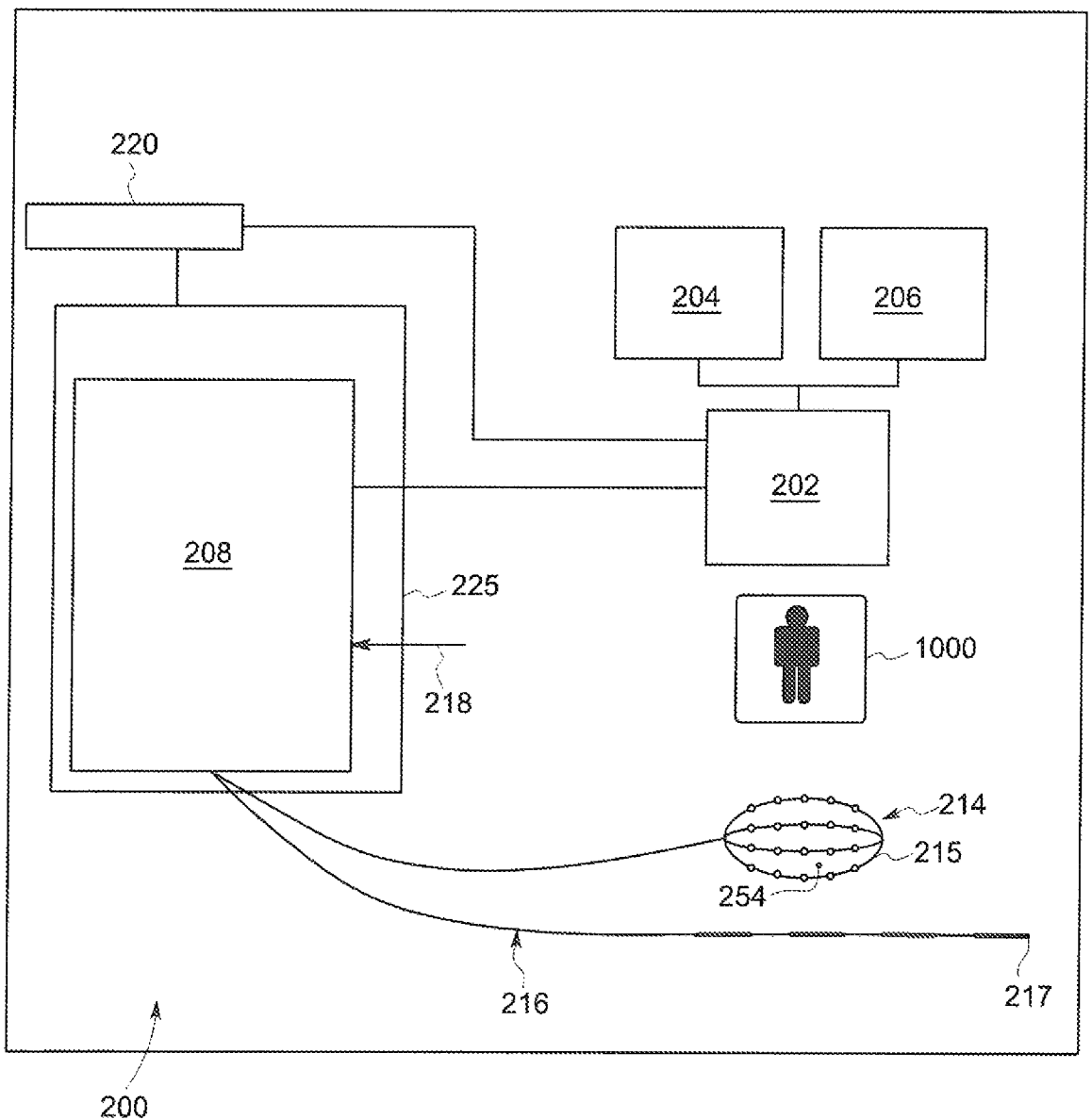
FIG. 1 is a schematic representation of a catheter navigation system using an EP mapping system constructed according to one exemplary embodiment of the present Invention.
Figure 2:
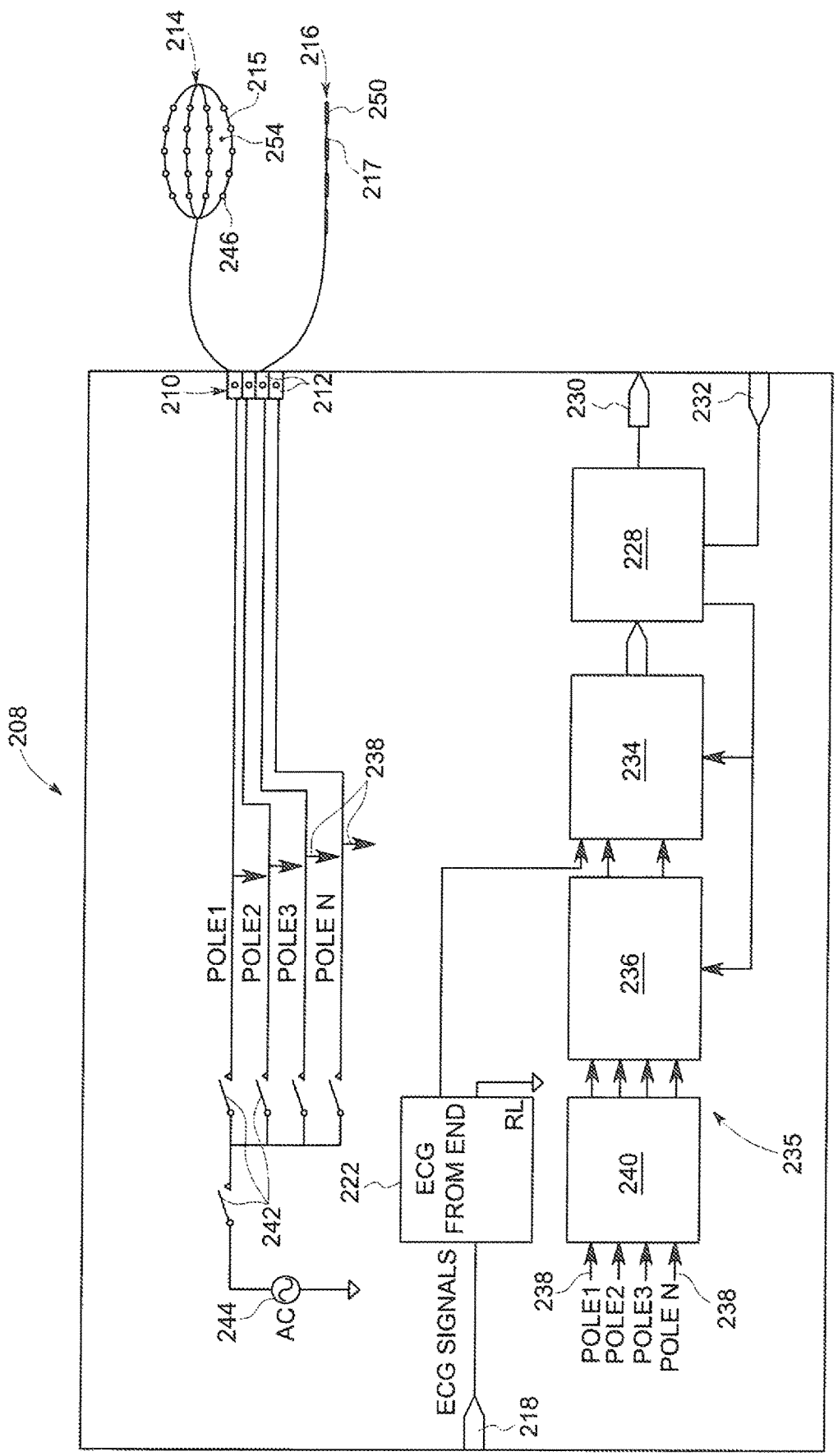
FIG. 2 is a schematic representation of an amplifier for the navigation system of FIG. 1 according to an exemplary embodiment of the invention.

FIGS. 1 and 2 illustrate one exemplary embodiment of a catheter navigation system 200 that utilizes an electrophysiology (EP) mapping system 220 with an EP recorder system 225, or other suitable 2D or 3D mapping system normally utilized to map larger areas or regions of interest to a procedure with the body 1000 of a patient. These systems 220,222 apply an electrical signal (e.g., electrical current) via catheters 214,216 to various locations of a subject's body 1000, such as the heart. The systems 220,225 can be similar to that disclosed in US Patent Application Publication No. US2013/0030482, which is expressly incorporated herein in its entirety. The systems 220,225 address a need to detect, and record a location and time of delivery of the electrical signal within the subject's heart and enables the generation of a display or graphic illustration of an electrical map on a display that shows a location of delivery of the signal via the catheters 214,215,216 to the subject's heart concurrent with a real time display of an electrocardiogram (ECG) (not shown) (e.g., surface and/or intracardiac) of the subject's heart during the delivery of the signal.

The mapping system 220 can be electrically connected to route the signal from the cardiac signal generator 244 to the catheter(s) 214,215 tracked by the mapping system 220 in applying the signal to various locations of the subject's heart as elected by the physician. The catheters 214,215 utilized in the mapping system 220 can include multiple traditional catheters 214, or a single basket catheter 215, each of which provide multiple electrodes 246 thereon through which the electrical signal can be directed to the particular region of tissue in the body, i.e., the heart, as selected by the physician. Examples of the mapping system 220 and catheters 214 can include CARTO 3 by Biosense Webster, EnSite NavX by St Jude Medical, etc. The mapping system 220 can be operable to communicate the signal via the catheter 214,215 to locations of the subject's heart and track locations of delivery of the signal and related electrical activity of the subject's heart associated therewith for illustration on a display. In addition to delivering the electrical signal to the subject's heart, the mapping system 220 can be connected to close the electrical circuit in such a manner to communicate the return electrical signal passing through the subject's heart for communication via the system 220 to the signal generator 244.

The EP recorder system 225 can be operable to acquire surface or intracardiac ECG signals of the subject's heart concurrent with application of the signal via the catheters 214,215 to the subject's heart and mapping of the subject's heart. Examples of the EP recorder system 225 can include CardioLab by General Electric Company, EP WorkMate by St Jude Medical, Lab System Pro by Boston Scientific) etc.

In FIG. 2, in one exemplary embodiment a modified construction of the system 200 includes a computer 202 operably connected to a real time display 204 and a review display 206, and to the amplifier 208 disposed in the EP recorder 225. The computer 202 is also connected to the EP mapping system 220, to enable use of the EP mapping system 220 in conjunction with the EP recorder 225 via the computer 202

In the illustrated exemplary embodiment, the amplifier 208 is operably connected via a terminal block 210 to a navigation catheter 214 terminating in a navigation or basket catheter tip 215 and a treatment catheter 216 terminating in an ablation catheter tip 217. The catheters 214,216 are engaged with a specific terminal 212 in the block 210 to enable identification of the catheters 214,216 and the signals being sent to or received from the catheters 214,216. The amplifier 208 also includes an input 218 for connection to the ECG leads (not shown) in order for ECG signals to be employed by the computer 202 in the operation of both the EP recording system 225 and EP mapping system 220. The ECG input 218 in the amplifier 208 includes an ECG front end 222 in which the signals from the ECG leads are received and conditioned for further processing by the system 200.

The amplifier 208 additionally includes a digital interface circuit 228 operably connected to each of a digital output 230 and a digital input or control 232, each of which are operably connected to the computer 202 to facilitate data sent between the amplifier 208/EP recorder 225 and the computer 202. The amplifier 208 also includes an analog-to-digital converter 234 connected between the ECG front end 222 and the digital interface circuit 232 to facilitate transfer of the ECG signals from the leads to the computer 202 for presentation in a suitable format on the display(s) 204,206.

Also connected to the A-D converter 234 is a signal generation network 235 used to initiate and direct the navigation signals to the desired catheter(s) 214,215. The network 235 can be a stimulation network utilized in exiting EP recorder amplifiers, but reconfigured to direct the navigation signals from the catheters 214,215 by switching out the existing stimulator generator associated with the stimulator network. The signal generation network 235 includes a cross-point switch matrix 236 to which is connected a number of conductors or leads 238 that pass through a low pass filter 240 prior to reaching the switch matrix 236 for noise reduction purposes. The interface circuit 228 is also operably connected to the switch matrix 236 such that the computer 202 can operate or control, i.e., send control signals, the network 235 via the circuit 228 to the switch matrix 236.

Opposite the filter 240 the leads 238 are each connected by an associated switch 242 between the signal generator/AC power source 244 an electrode 246 disposed on one of the catheters 214,215. The AC power source 244 takes the place of the stimulator generator in the stimulator network of the prior EP recorder amplifier. The number of leads 238 corresponds to the number of electrodes 246 disposed on the poles of the traditional catheters 214 or on the splines 219 of the basket catheter 215, such that the power from source 244 can be individually supplied to each of the electrodes 246. With this configuration of the amplifier 208 in the EP recorder 225, the stimulation network 235 allows the user via the computer or controller 202 to select individual electrodes 246 on the catheter 214,215 and thus route a navigation signal to the appropriate electrodes 246 via the switch matrix 236. In this micro-navigation system 200, the input to the stimulator network 235 can be switched from stimulation routing, to navigation by switching out the stimulator generator for an alternating constant current source 244. This is current from the source 244 is limited to less than 5-10 μA to avoid any risk of un-intended fibrillation by the signal generated at the selected electrode 246. Further, the signal source 244 may be dynamically modulated further such that it provides a series of pulsed bursts of navigation signals from the electrodes 246 on the catheters 214,215. In another exemplary embodiment of the invention, the pulsed modulated waveform of the navigation signal from the electrode 246 can be synchronized with the patients R-wave using the ECG signals received by the amplifier 208 to select the optimum transmission period. The treatment catheter 217 is then directed to the region of interest using conventional XRAY Fluor methods.

Regardless of the form taken by the signal, when generated at the selected electrode 246, the signal is detected by one or more electrodes 250 located on the treatment catheter 216 or ablation catheter 217 disposed near the point or region of interest, such as a by a Wheatstone bridge type structure, or a similar electrical signal detection structure operably connected to the detection electrode(s) 250, e.g., which can be located within the controller 202. Upon detection of the signal from the electrode 246 on the navigation catheter 214 by the detection structure via the detection electrode 250 on the treatment catheter 216, depending on the conduction level at the electrode 250, the catheter 216 can be moved in a direction to increase the conduction, indicating that the treatment catheter 216 is navigating towards the point or area/region of interest identified by the electrode 246. In the exemplary embodiment where the navigation catheter 214 takes the form of multiple traditional catheters 214 or a basket catheter 215, two or more electrodes 246 can be utilized to send signals to the electrodes 250 on the treatment catheter 216. The treatment catheter 216 can then be moved in a direction to the mid-point or null point of the conduction between the signal electrodes 246, indicating the point or area/region of interest.

To assist a physician in determining this position for the treatment catheter 216, various forms of visual indicators on the associated displays 204,206 may be employed such that the physician using the system 200 can visually determine the mid-point or null position for the treatment catheter 216. For example, on the display 204,206 various sounds, animated screen icons such as a ball, or changes of color in an identified area of an image of the mapped area within which the treatment catheter 216 is positioned—i.e. from white to black may be employed to indicate the location of the source of the point or area of interest, i.e., the arrhythmia.

A further enhancement to the visual representation of the electrodes 246,250 or catheters 214,216 on the display 204,206 may be made by allowing the user, or through automation, to highlight the energized electrodes 246 on the basket or mapping catheters 214 such that the treatment catheter 216 and electrode 250 can be directed or navigated towards the highlighted electrodes 246 on the display 204, 206.

In addition, the tip 252 of the treatment or ablation catheter 216,217 can be detected by its shape and/or other characteristic properties such that the tip 252 (FIG. 3) can be highlighted in a different color on the display 204 showing the mapped region of interest, such that the position of the tip 252 relative to the selected and energized electrodes 246 is clearly visible. With these visual enhancements to the system 200, in an exemplary embodiment of the invention the user can confidently direct the ablation catheter 217 to the region of interest without the use of a conventional electro-anatomical mapping system.

When using the system 200, the accuracy of the positioning of the treatment catheter 216 is greater than the size of the tip 252 of the treatment catheter 216, which is typically 4-8 mm. Instead, the accuracy of the positioning of the tip 252 is limited to the accuracy of the detection bridge structure in the electrodes 250, and the associated tolerance of the signal capture. Thus, an accuracy of 0.01 to 0.001 decimal places is expected, which is significantly less than the size of the catheter tip 252, and which should provide a much more effective and precise treatment from the treatment catheter 216.

Figure 3:
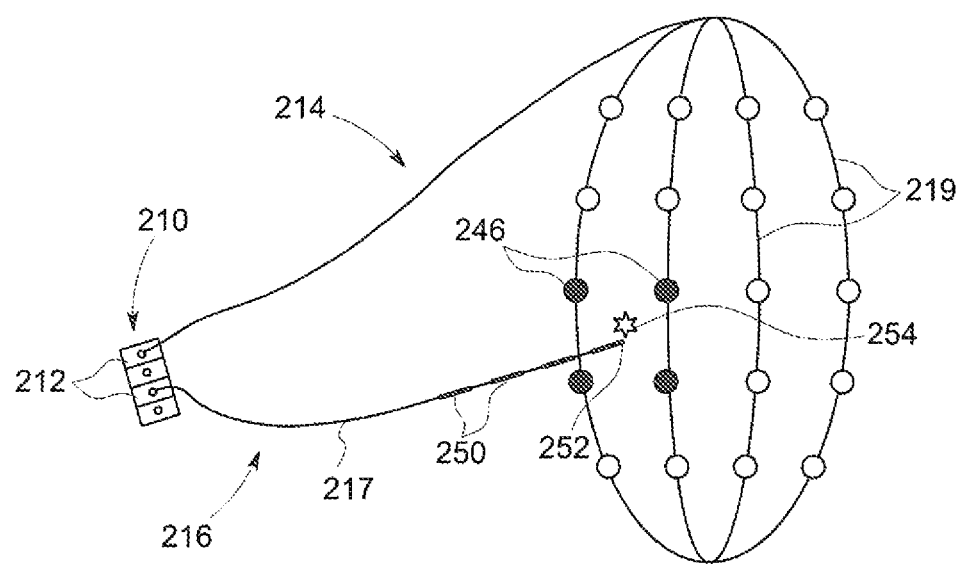
FIG. 3 is a schematic representation of the navigation of a treatment catheter using a basket catheter according to one exemplary embodiment of a method of using the system of the present invention.

In operation, referring now to the exemplary embodiment of FIG. 3, the system 200 uses the coordinates obtained by the mapping system 220 relative to the electrodes 246 on either a basket catheter 215 or multiple mapping catheters 214 to provide very localized navigation within the region or area of interest bounded by the electrodes 246, Initially, using imaging visualization employed for macro navigation to initially determine the region of interest, including conventional imaging techniques such as rotational angiography, computed tomography, or even ultrasound, for example, the navigational catheter(s) 214,215 is/are positioned at the region of interest as determined by the imaging visualization technique. A set of coordinates for the point or area of interest 254 are then determined h a 2D or 3D mapping system, or through conventional EP mapping method/system 220 for the region of interest to be identified in the study. To navigate the treatment catheter 216, e.g., ablation catheter 217, to these identified coordinates, the system 200 can either take this information from the mapping system 220, or have the information manually entered by a user, to select the appropriate electrodes 246 on the navigation catheter(s) 214,215. Further, as a result of the small localized detection/navigation signals or series of signals emitted by the system, the system 200 can be used for micro-navigation of the treatment catheter 216,217 in and immediately around the point or region of interest 254, but cannot be utilized to map larger regions, such as an entire chamber of the heart, or to model the interior of the heart, which is necessarily done using conventional imaging techniques.

Once the coordinates and corresponding electrodes 246 on the navigation catheter(s) 214,215 have been determined, the treatment catheter 216 is positioned approximate the area of interest, such as within the region around the area of interest 254 as illustrated on the display 204, 206. At that point, a series of very small localized navigation signals may be provided to the selected electrodes 246 on the navigation catheter 214, such that the treatment catheter 216 can than be "centered" on the point or region of interest 254, such as within the chamber of the heart. In the exemplary embodiment of FIG. 3, the navigation catheter 214,215 is operated by applying electric signals to four (4) electrodes 246, where the selected electrodes 246 form four (4) poles surrounding the point of interest 254. The signals applied to these electrodes 246 each have a different frequency, such that the treatment catheter 216,217 can receive those signals and interpolate the strength of the respective signals from the electrodes 246 in a known manner to locate the point of interest 254 that is bounded by the 4 poles defined by the energized electrodes 246. In an alternative exemplary embodiment, the signal can be applied to the treatment catheter 216,217 and read/detected by the 4 poles defined by the electrodes 246 on the navigation catheter 214,215 and interpolated in a known manner to direct the treatment catheter 216,217 to the point or area of interest 254 bounded by the poles.

According to other alternative embodiments, the system 200 can potentially be employed with other suitable modes for proximity detection of the treatment catheter 216,217 relative to the navigation catheter 214,215. For example, the system 200 can employ the use of the navigation catheter 214,215 with the treatment catheter 216,217 in conjunction with a system for matching the signal template to correlate the signal from the navigation catheter 214,215 to the source arrhythmia pattern, such as to confirm the area or position of interest to be treated. Also, the signals can alternatively be emitted by the electrodes 250 on the treatment catheter 216,217 and received by the electrodes 246 on the navigation catheter 214,215.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system to navigate a treatment catheter to an area of interest to be treated in a body of a patient, the system comprising:
   a navigation catheter including a number of first electrodes thereon positionable around the area of interest;
   a treatment catheter including a number of second electrodes thereon;
   an electrical signal detection structure;
   a controller operably connected to the navigation catheter and the treatment catheter to selectively energize at least one of the first electrodes to emit at least one navigation signal from a specific location within the area of interest; and
   a signal generator operably connected to the number of first electrodes to energize the selected first electrode to emit the at least one navigation signal, and wherein the at least one navigation signal is emitted from the selected first electrode using a current from the signal generator of less than 5 to 10 microamperes;
   wherein at least one of the second electrodes is coupled to the electrical signal detection structure that is configured to detect the at least one navigation signal and enable the treatment catheter to be moved towards the specific location within the area of interest where an increasing conduction level at the at least one of the second electrodes indicates that the treatment catheter is navigating towards the area of interest, the area of interest being a location of any of the first electrodes energized to emit the at least one navigation signal.

2. The system of claim 1 wherein the controller is an EP mapping or recorder system including a stimulation network configured to selectively energize the number of first electrodes to emit the at least one navigation signal.

3. The system of claim 1 wherein the navigation catheter includes a number of catheters, each navigation catheter having a number of first electrodes thereon.

4. The system of claim 1 wherein the navigation catheter is a basket catheter.

5. The system of claim 1 wherein the treatment catheter is an ablation catheter.

6. The system of claim 1 further comprising a display operably connected to the controller and configured to visually represent the relative positions of the navigation catheter and the treatment catheter.

7. The system of claim 6 wherein the display visually represents the relative positions of the energized electrodes and the treatment catheter.

8. The system of claim 6 wherein the controller is a EP mapping system and wherein the display for the relative positions of the navigation catheter and the treatment catheter are displayed on a map of the area of interest from the EP mapping system.

9. The system of claim 1 wherein the navigation catheter includes at least four (4) first electrodes to define four (4) poles around the area of interest.

10. The system of claim 9 wherein the at least one navigation signal is emitted from the at least four (4) first electrodes.

11. A system to navigate a treatment catheter to an area of interest to be treated in a body of a patient, the system comprising:
  a navigation catheter including at least two first electrodes thereon positionable around the area of interest;
  a treatment catheter including a number of second electrodes thereon;
  an electrical signal detection structure;
  a controller operably connected to the navigation catheter and the treatment catheter to selectively energize at least two of the first electrodes to emit respective navigation signals from a specific location within the area of interest; and
  a signal generator operably connected to the number of first electrodes to energize the at least two of the first electrodes to emit the navigation signals, and wherein the navigation signals are emitted from the at least two of the first electrodes using a current from the signal generator of less than 5 to 10 microamperes;
  wherein at least one of the second electrodes is coupled to an electrical signal detection structure that is configured to detect the navigation signals and enable the treatment catheter to be moved towards the specific location within the area of interest identified as a mid-point or null point of conduction between two or more first electrodes energized to emit the respective navigation signals.

* * * * *